United States Patent [19]

Bell et al.

[11] Patent Number: 4,761,371

[45] Date of Patent: Aug. 2, 1988

[54] INSULIN RECEPTOR

[75] Inventors: John R. Bell, San Francisco; Janakiraman Ramachandran, Palo Alto; Axel Ullrich, San Francisco, all of Calif.

[73] Assignee: Genentech, Inc., South San Francisco, Calif.

[21] Appl. No.: 700,776

[22] Filed: Feb. 12, 1985

[51] Int. Cl.[4] .................. C12P 21/00; C12P 19/34; C12N 15/00; C07H 15/12
[52] U.S. Cl. .................. 435/68; 435/70; 435/91; 435/172.3; 435/320; 536/27; 935/29; 935/32; 935/56
[58] Field of Search .......... 435/68, 70, 91, 172.3, 435/235, 317, 253; 536/27; 935/32, 29, 54, 56, 60, 70, 72

[56] References Cited

PUBLICATIONS

Petruzzelli, L., et al., "Proc. Natl. Acad. Sci. USA" 81: 3327–3331 (Jun. 1984).

Cobb, M. H. et al. "Biochim. et Biophys. Acta" 738: 1–8 (1984).
Ullrich et al., (1984) *Nature*, vol. 309, pp. 418–425.
Downward et al. (1984) *Nature*, vol. 307, pp. 521–527.
Siegel et al. (1981) *J. Biol. Chem.*, vol. 256, pp. 9266–9273.
King et al. (1982) *J. Biol. Chem.*, vol. 2257, pp. 10869–10873.

*Primary Examiner*—Thomas G. Wiseman
*Assistant Examiner*—Stephanie Seidman

[57] ABSTRACT

Insulin receptor is purified in accordance with this invention to a level sufficient to enable amino acid sequencing thereof. DNA encoding insulin receptor is provided, as well as methods for synthesizing insulin receptor or its mutant in heterologous host cells transformed with vectors containing such DNA. Knowledge of the amino acid sequence for insulin receptor enables the preparation of novel immunogenic conjugates and antibodies raised against such conjugates. Novel therapeutically useful forms of the insulin receptor and anti-receptor antibodies are described.

13 Claims, 14 Drawing Sheets

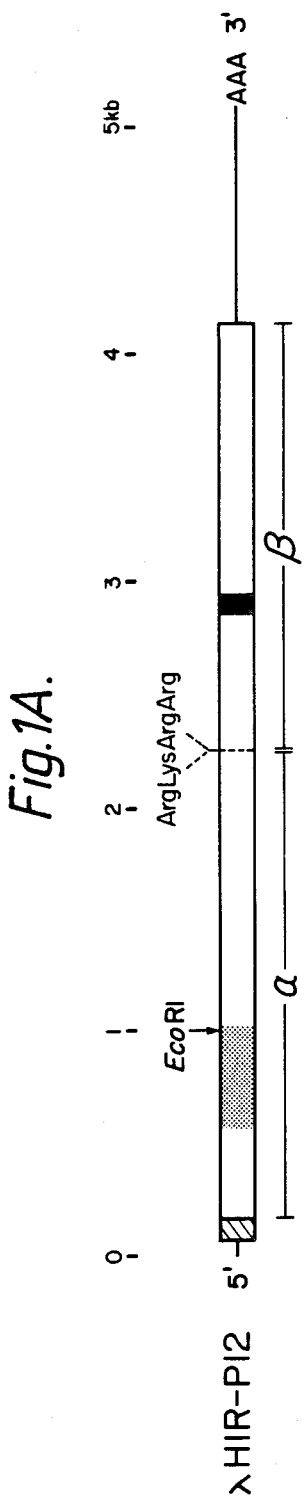

Fig. 1B(I)

```
                                                                                                              150
ACCGGGAGGCGCGCTCTGATCCGAGGAGACCCCGCGCTCCCGCAGCAGGCCACCGGGCACCGGGGCCGGCGGGGGCG
                      -27
                        MetGlyThrGlyGlyArgArgGlyAla
                                          -20
                                                                        → α subunit
                                                                    -1  1
        -10
AlaAlaAlaProLeuLeuValAlaValAlaAlaLeuLeuGlyAlaAlaGlyHisLeuTyrProGlyGluVal
GCGGCCGCGCCGCTGCTGGTGGCGGTGGCCGCCCTGCTGGGCGCCGCCGGGCACCTGTACCCCGAGAGGTG
                                                                                                              300
           10                        20                      30
  ProGlyMetAspIleArgAsnAsnLeuThrArgLeuHisGluLeuGluHisGluLeuGlyGluLeuArgGluThrLeuGlyProIleGlyHis
                                                        SerValIleGlyHis
   CCCGGCATGGATATCCGGAACAACCTCACTAGGTTGCATGAGCTGGAGATTGCTCTGTCATCGAAGGACAC
                40                                  50
LeuGlnIleLeuLeuMetPheLysThrArgProGluAspPheArgAspLeuSerPheProLysLeuIleMetIle
TTGCAGATACTCTTGATGTTCAAAACGAGGCCCGAAGATTTCCGAGACCTCAGTTTCCCCAAACTCATCATGATC
                                                                                                              450
          60                                  70
ThrAspTyrLeuLeuLeuPheArgValTyrGlyLeuLeuGluSerLeuLysAspLeuPheProAsnLeuThrValIle
ACTGATTACTTGCTCTTCCGGGTCTATGGGCTCCTGGAGAGCCTGAAGGACCTGTTCCCCAACCTCACGGTCATC
               90                               100
ArgGlySerArgArgLeuPhePheAsnTyrAlaLeuValIlePheGluMetValHisSerLeuLysGluLeuLeuTyr
CGGGGATCACGACTGTTCTTTAACTACGCGGCTGGTCATCTTCGAGATGGTTCACCTCAAGGAACTCGGCCTCTAC
                                                                                                              600
                 110                               120                             130
AsnLeuMetAsnIleThrArgGlySerValArgIleGluLysAsnAsnGluLeuTyrLeuAlaThrIleAsp
AACCTGATGAACATCACCCGGGGTTCTGTCCGCATCGAGAAGAACAATGAGCTCTATCTCGCCACTATCGAC
                140                                  150
TrpSerArgIleLeuAspSerValGluAspAsnTyrIleValLeuAsnLysAspAsnGluCysGlyAsp
TGGTCCCGTATCCTGGATTCCGTGGAGGATAATTACATCGTGTTGAACAAAGATGACAACGAGTGTGGAGAC
```

Fig. 1B(II)

```
        160                        170                              180
IleCysProGlyThrAlaLysGlyLysThrAsnGlyAlaThrValIleAsnGlyGlnPheValGluArgCys
ATCTGTCCGGGTACCGCGAAGGGCAAGACCAACGGCGCCACCGTCATCAACGGGCAGTTTGTCGAACGATGT    750

190                        200
TrpThrHisSerHisCysGlnLysLysValCysProThrIleCysLysSerHisGlyLysThrAlaGluGlyLeuCys
TGGACTCATAGTCACTGCCAGAAAGTTTGCCCGACCATCTGTAAGTCACACGGCAAGACCGCCGAAGGCCTCTGT 210                        220                        230
CysHisSerGluCysLeuGlyAsnCysSerGlnProAspAspProThrLysCysValAlaAlaCysArgAsnPheTyr
TGCCACAGCGAGTGCCTGGGCAACTGTTCTCAGCCCGACGACCCCACCAAGTGTGTGGCCGCCTGCCGCAACTTCTAC    900

240                        250
LeuAspGlyArgCysValGluHisThrCysProProTyrTyrHisPheGlnAspTrpArgCysValAsnPheSer
CTGGACGGGCAGGTGTGTGGAGCACACCTGCCCGCCCTACTACCACTTCCAGGACTGGCGCTGTGTGAACTTCAGC 260                        270                        280
PheCysGlnAspLeuHisHisLysCysLysAsnSerArgArgGlnGlyCysHisGlnTyrValIleHisAsnAsn
TTCTGCCAGGACCTGCACCACAAATGCAAGAACTCGCGGAGGCAGGGCTGCCACCAGTACGTCATTCACAACAAC 290                        300                   1050
LysCysIleProGluCysProSerGlyTyrThrMetAsnSerSerAsnLeuCysThrProLeuGlyPro
AAGTGCATCCCTGAGTGTCCCTCCGGGTACACGATGAATTCCAGCAACTTGTGTACCCCCATTGGTCCC 310                        320                        330
CysProLysValCysHisLeuLeuGluGlyGluLysThrIleAspSerValThrSerAlaGlnGluLeuArgGly
TGCCCCAAGGTGTGCCACCTCCTAGAAGGCGAGAAGACCATCGACTCGGTGACGTCGCCCAGGAGCTCGAGGA 340                        350                   1200
CysThrValIleAsnGlySerLeuIleIleAsnIleArgGlyGlyAsnAsnLeuAlaAlaGluLeuAlaAsn
TGCACCGTCATCAACGGGAGTCTGATCATCAACATTCGAGGAGGCAACAATCTGGCAGCTGAGCTAGAAGGCCAAC
```

Fig. 1B(III)

```
                                    360                                           370                                          380
                    LeuGlyLeuIleGluGluIleSerGlyTyrLeuLysIleArgArgSerTyrAlaLeuValSerLeuSerPhePhe
                    CTCGGCCTCATTGAAGAGAATTTCAGGGTATCTAAAAATCCGCGATCCTACGCTCTGGTGTCACTTTCCTTCTTC    1350
                                       390                                          400
                    ArgLysLeuArgLeuIleArgGlyThrLeuGluIleGlyLyAsnTyrSerPheTyrAlaLeuAspAsnGlnAsn
                    CGGAAGTTACGTCTGATTCGAGGAGAGACCTTGGAAATTGGGAACTACTCCTTCTATGCCTTGGACAACCAGAAC
                                        410                                          430
                    LeuArgGlnLeuTrpSerLysHisAsnLeuThrIleThrGlnGlyLysLeuPhePheHisTyrAsnPro
                    CTAAGGCAGCTCTGGGACTGGAGCAAAACACAACCTCACCATCACTCAGGGGAAACTCTTCTTCCACTATAACCCC
                                        440                                          450
                    LysLeuLysLeuSerGluIleHisLysMetGluGluValSerGlyThrLysGlyThrArgGlnArgAsnAspIle    1500
                    AAACTCTGCTTGTCAGAAATCCACAAGATGGAAGAAGTTTCAGGAACCAAGGGGCGCCAGGAGAGAAACGACATT
                                        460                                          470
                    AlaLeuLysThrAsnGlyAspGlnAlaSerCysGluAsnGlyLeuLeuLysPheSerTyrIleArgThrSerPhe
                    GCCCTGAAGACCAATGGGGACCAGGCATCCTGTGAAAATGAGTTACTTAAATTTTCTTACATTCGGACATCTTTT
                                        490                                          500
                    AspLysIleLeuLeuArgTrpGluProTyrTrpProProAspPheArgAspLeuLeuGlyPheMetLeuPheTyr    1650
                    GACAAGATCTTGCTGAGATGGGAGCCGTACTGGCCCCCGACTTCCGAGACCTCTTGGGGTTCATGCTGTTCTAC
                                        510                                          520                                          530
                    LysGluAlaProTyrGlnAsnValThrGluPheAspGlnAsnAlaCysGlySerAsnSerTrpThrValVal
                    AAAGAGGCCCCTTATCAGAATGTGACGGAGTTCGACGGCAGGATGCATGTGGTTCCAACAGTTGGACGGTGGTA
                                        540                                          550
                    AspIleAspProLeuArgSerAsnAspProLysGlnAsnHisProGlyTrpLeuMetArgGlyLeuLys           1800
                    GACATTGACCCCCTGAGGTCAACGACCCCAAATCACAGAACCACCCAGGGTGGCTGATGCGGGGTCTCAAG
```

Fig. 1B(IV)

```
       560                          570                         580
ProTrpThrGlnTyrAlaIlePheValLysThrLeuValThrPheSerAspGluArgArgThrTyrGlyAlaLys
CCCTGGACCCAGTACGCCATTGTTTGTGAAGACCCTGGTCACCTTTTCGGATGAACGCCGGACCTATGGGCAAG
                                                                               1950

SerAspIleIleTyrValGlnThrAspAlaThrAsnProSerValProLeuAspProIleSerValSerAsnSer
AGTGACATCATTTATGTCCAGACAGATGCCACCAACCCCTCTGTGCCCCTGGATCCAATCTCAGTGTCTAACTCA
      610                         620                          630
SerSerGlnIleIleLeuLysTrpLysProProSerAspProAsnGlyAsnIleThrHisTyrLeuValPheTrp
TCATCCCAGATTATTCTGAAGTGGAAACCACCTTCCGACCCCAATGGCAACATCACCCACTACCTGGTTTTCTGG
                                  650                           2100
GluArgGlnAlaGluAspSerGluLeuPheGluLeuAspIleLysTyrCysLeuLysLeuProSerArgThr
GAGAGGCAGGCGGAAGACAGTGAGCTGTTCGAGCTGGATATTAAGTACTGCCTCAAAGGGCTGAAGCCCTCGAGGACC
      660                          670                          680
TrpSerProProPheGluSerGlyGluAspSerGlnLysHisAsnGlnSerGluTyrGluAspSerAlaGlyLysCys
TGGTCTCCACCATTCGAGTCTGGAGAAGACAGTCAGAAGCACAACCAGAGTGAGTATGAGGATTCGGCGGGAAATGC
                                   700                           2250
CysSerCysProLysThrAspSerGlnIleLeuLysGluLeuGluGluSerPheArgLysThrPheGluAsp
TGCTCCTGCCCCAAAGACAGACTCTCAGATCCTGAAGGAGCTGGAGGAGTCCTTTAGGAAGACAGTTTGAGGAT
                                                            β subunit
TyrLeuHisAsnValValPheValProArgProSerArgLysArgArgSerLeuGlyAspValGlyAsnValThr
TACCTGCACAACGTGGTTTTCGTCCCCAGGCCATCTCGGAAACGCAGGTCCCTTGGCGATGTTGGGAATGTGACG
                                                                                2400
ValAlaValProThrValAlaPheProAsnThrSerSerValProThrSerProValProThrSerProValProThrSerProGluHisArg
GTGGCCGTGCCCACGGTGCCCAGCTTCCCAACACTTCCTGACCAGCTGCCCAGTCCGAGGAGCACAGG
```

Fig. 1B(V)

```
              760                                            770                                            780
ProPheGluLysValValAsnLysGluSerLeuValIleSerGlyLeuLeuArgHisPheThrGlyTyrArgIleGlu
CCTTTTGAGAAGGTGTGAACAAGGAGTCGCTGGTCATCTCCGGCTTGCTGCGACACTTCACGGGCTATCGCATCGAG  2550
                        790                                  800
LeuGlnAlaCysAsnGlnAspThrProGluGluArgLysSerValAlaAlaTyrValSerAlaArgThrMetPro
CTGCAGGCTTGCAACCAGGACACCCCTGAGGAACGGAAGTCAGTGGCAGCCTACGTCAGTGCGAGGACCATGCCT
              810                                            820                                            830
GluAlaLysArgAlaAspAspIleValGlyProValThrHisGlyIlePheGluAsnAsnValValHisLeuMetTrp
GAAGCCAAGCGTGATGACATTGTGGCCCTGTGACGCATGAAATCTTTGAGAACAACGTCGTCCACTTGATGTGG
                        840                                            850
GlnGluProLysGluProAsnGlyLeuLeuIleValLeuSerTyrArgArgTyrGlyAspGlyGluLeu
CAGGAGCCGAAGGAGCCCAATGGTCTGATCGTGCTGTATCGGCGATATGGTGATGAGGAGCTG              2700
              860                                            870                                            880
HisLeuCysAspThrArgLysHisPheAlaLeuArgLeuArgGlyAlaArgGlyLeuArgGlyLeuAsnTyr
CATCTCTGCGACACCCGCAAGCACTTCGCTCTGGAACGGCTGCGTGGGGCTGTCACCGGGGAACTAC
                        890                                  900
SerValArgIleArgAlaThrSerLeuAlaGlyLysAsnGlySerTrpThrGluProThrTyrPheTyrValThrAsp
AGCGTGCGAATCCGGGCCACCTCCCTTGCGGGCAAGCGTCTTGGACGGAACCCACCTATTTCTACGTGACAGAC  2850
              910                                            920                                            930
TyrLeuAspValProSerAsnIleAlaLysIleIleGlyIleProLeuIlePheValPheLeuPheSerValVal
TATTTAGACGTCCCGTCAAATATTGCAAAATATCATCGGCCCCCTCATCTTTGTCTTTCTTCAGTGTGTG
                        940                                            950
IleGlySerIleTyrLeuPheLeuArgLysArgGlnProLeuGlyProAspGlyProLeuTyrAlaSerSerAsn
ATTGGAAGTATTTATCTATTCCTGAGAAAGAGGCAGCCAGATGGCCGCTGGACCGCTTTACGCTTCTTCAAAC    3000
```

Fig. 1B(VI)

```
             960                               970                               980
ProGluTyrLeuSerAlaSerAspValPheProCysSerValTyrValProAspGluTrpGluValSerArgGlu
CCTGAGTATCTCAGTGCCAGTGATGTTTCCATGCTCTGTGTACGTGCCGGACGAGTGGGAGGTGTCTGAGAG           3150

990                              1000
LysIleThrLeuLeuArgGluLeuGlyInGlySerPheGlyMetValTyrGluGlyAsnAlaArgAspIleIle
AAGATCACCCTCCTTCGAGAGCTGGGGCAGGGCTCCTTCGGCATGGTGTATGAGGGCAATGCCAGGGACATCATC 1010                              1020                             1030
LysGlyGluAlaGluArgValAlaValLysThrValAsnGluSerAlaSerLeuArgGluArgIleGluPhe
AAGGGTGAGGCAGAGAGACCCGTGGCGGTGAAGACGGTCAACGAGTCAGCCAGTCTCCGAGAGCGGATTGAGTTC       3300

1040                             1050
LeuAsnGluAlaSerValMetLysGlyPheThrCysHisHisValValArgLeuLeuGlyValValSerLysGly
CTCAATGAGGCCTCGGTCATGAAGGGCTTCACCTGCCATCACGTGGTGCGCCTCCTGGGAGTGGTGTCCAAGGGC 1060                            1070                             1080
GlnProThrLeuValMetGluLeuMetAlaHisGlyAspLeuLysSerTyrLeuArgSerLeuArgProGlu
CAGCCCACGCTGGTGATGGAGCTGATGGCCCACGGAGACCTGAAGAGCTACCTCCGTTCTCTGCGGCCAGAG 1090                           1100                            1110
AlaGluAsnAsnProGlyArgProProProThrLeuGlnGluMetIleGlnMetAlaAlaGluIleAlaAspGly
GCTGAGAATAATCCTGGCCGCCCCTCCCCCACCCTTCAAGAGATGATTCAGATGGCGGCAGAGATTGCTGACGGG   3450

1120                            1130
MetAlaTyrLeuAsnAlaLysLysPheValHisArgAspLeuAlaAlaArgAsnCysMetValAlaHisAspPhe
ATGGCCTACCTGAACGCCAAGAAGTTTGTGCATCGGGACCTGGCAGCGAGAAACTGCATGGTCGCCCATGATTTT 1140                            1150
ThrValLysIleGlyAspPheGlyMetThrArgAspIleTyrGluThrAspTyrTyrArgLysGlyGlyLysGly
ACTGTCAAAATTGGAGACTTTGGAATGACCAGAGACATCTATGAAACGGATTACTACCGGAAGGGGGCAAGGGT   3600
```

Fig. 1B(VII)

```
              1160                                           1170                                           1180
LeuLeuProValArgTrpMetAlaProGluSerLeuLysAspGlyValPheThrThrSerSerAspMetTrpSer
CTGCTCCCTGTACGGTGGAGGCACCGGAGTCCCTGAAGGATGGGGTCTTCACCACTTCTTCTGACATGTGGTCC      3750

1190                                           1200
PheGlyValValLeuTrpGluIleThrSerLeuAlaGluGlnProTyrGlnGlyLeuSerAsnGluGlnValLeu
TTTGGCGTGGTCCTTTGGGAAATCACCAGCTTGGCAGAACAGCCTTACCAAGGCCTGTCTAATGAACAGGTGTTG 1210                                           1220                                           1230
LysPheValMetAspGlyTyrLeuAspIleAspAspAsnLysCysValProGluArgValThrAspLeuMetArgMet
AAATTTGTCATGGATGGGTATCTGGATCAACCCGACAACTGTGTCCAGAGAGAGTCACTGACCTCATGCGCATG 1240                                           1250
CysTrpGlnPheAsnProAsnMetArgProThrPheLeuGluIleValAsnLeuLeuLysAspLeuHisPro
TGCTGGCAATTCAACCCAACATGAGGCCAACTTCCTGGAGATTGTCAACCTGCTCAAGGACCTGCACCCC       3900

1260                                           1270                                           1280
SerPheProGluValSerPhePheHisSerGluAspLysAsnLysAlaProGluSerGluGluLeuGluMetGluPhe
AGCTTTCCAGAGGTGTCGTTCTTCCACAGCGAGGACAAGAACAAGGCTCCCGAGAGTGAGGAGCTGGAGATGGAGTTT 1290                                           1300
GluAspMetGluAsnValProLeuAspArgSerSerHisCysGlnArgGluGluAlaGlyGlyArgAspGlyGly
GAGGACATGGAGAATGTGCCCCTGGACCGTTCCTCGCACTGTCAGAGGGAGGAGGCGGGGGGCCGGGATGGAGGG      4050

1310                                           1320                                           1330
SerSerLeuGlyPheLysArgSerTyrGluGluHisIleProTyrThrHisMetAsnGlyGlyLysLysAsnGly
TCCTCGCTGGGTTTCAAGCGGAGCTACGAGGAGCACATCCCTTACACACACATGAACGGAGGCAAGAAAAACGGG

ArgIleLeuThrLeuProArgSerAlaAsnProSerEnd
CGGATTCTGACCTTGCCTCGGTCCAATCCTTCCTAACAGTGCCTACCGTGGCGGGGGCGGGCAGGGGTTCCCATT       4200
                                1340
```

Fig. 1B(VIII)

```
TTCGCTTTCCTCTGGTTTGAAAGCCTCTGGAAAACTCAGGATTCTCACGACTCTACCATGTCCAATGGAGTTCAG
AGATCGTTCCTATACATTTCTGTTCATCTTAAGGTGGACTCGTTTGGTTACCAATTTAACTAGTCCTGCAGAGGA      4350
TTTAACTGTGAACCTGAGGGCAAGGGGTTTCCACAGTTGCTGCTCCTTTGGGCAACGACGTTTCAAACCAGG
ATTTGTGTTTTTTTTCGTTCCCCCACCCGCCCCCAGCAGAAGCACCTGTTTTACAAATTCTTTTT                4500
TTTTTTTTTTTGCTGGTGTCTGAGCTTCAGTATAAAAGACAAACTTCCTGTTTGTGGAACAAAAGTTCG
AAAGAAAAACAAAACAAAACACCCAGCCTGTTCCAGGAGAATTTCAAGTTTACAGGTTGAGCTTCAAGATG         4650
GTTTTTTGGTTTTTTTTTTCTCTCATCCAGGCTGAAGGATTTTTTTTCTTTACAAAATGAGTTCCTCAAA
TTGACCAATAGCTGCTGCTTTCATATTTGGATAAGGGTCTGTGGTCCGGTGCTCACGTGTGTATGCACG           4800
TGTGTGTCCATTAGACACGGCTGACGTGTGCAAAGTATCCATGCGGAGTTGATGCTTTGGGAATTGGCTCA
TGAAGGTCTTCTCAAGGGTGCGAGCTCATCCCCCTCTCTCTCTCACCCTCAGGTTCTACCCTCCCTCACATTGGTGCCAAGGGAGGAGCA    4950
ACAGATTCTCTGTGTCAGAAGTCTAGCTCAGGTTCTACCCTCCCTCACATTGGTGCCAAGGGAGGAGCA
TTTCATTTGGAGTGATTATGAATCTTTCAAGACCAAACCAAGCTAGGACATTAAAAAAAAAAAGAAAAGA           5100
AAGAAAAAAACAAAATGGAAAAAGGAAAAAAAAAAAAAGAACTGAGATGACAGAGTTTGAGAATATATTTGTACCAT
ATTTAAAAAAAAAAAAAAAAA
```

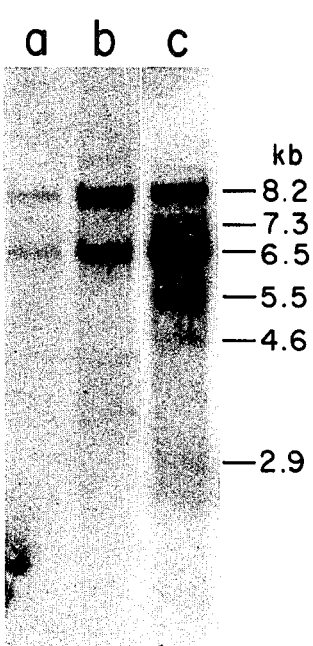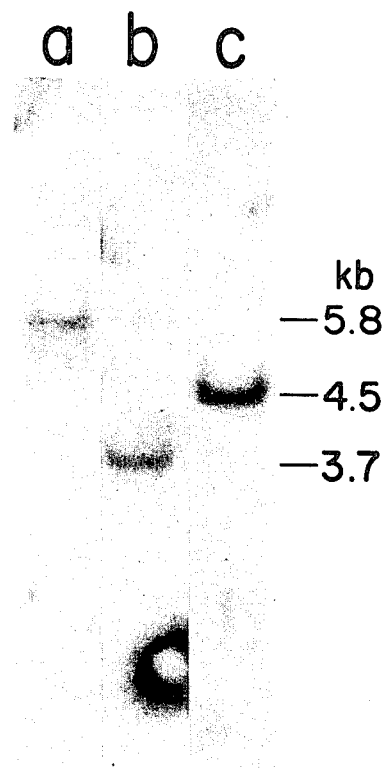
Fig. 2A.
Fig. 2B.

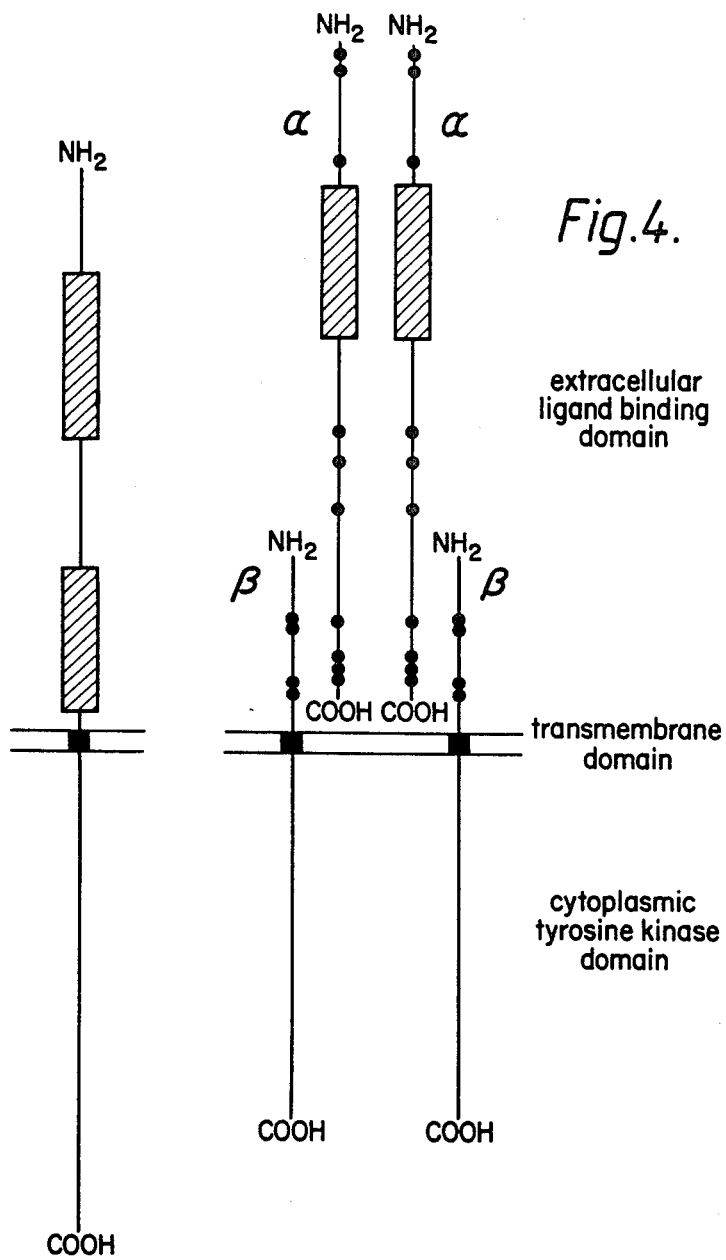

INSULIN RECEPTOR

BACKGROUND INFORMATION

This relates to the mammalian insulin receptor. In particular it relates to the synthesis of the insulin receptor by recombinant cells and to the manufacture and use of certain novel products enabled by the identification and cloning of DNA encoding the insulin receptor.

The rapid matabolic effects of insulin as well as its long term growth promoting actions are initiated by the interaction of the hormone with specific, high affinity cell surface receptors[1-3]. The indulin receptor (apparent $M_r$ 350,000–400,000) is an integral membrane glycoprotein composed of two α subunits (apparent $M_r$=120,000–130,000) and two β subunits (apparent $M_r$=90,000), which are linked by disulfide bonds [4-8]. Photoaffinity labelling of the receptor[9,10] as well as affinity cross linking[7,11] have shown that the α submit is predominantly labelled by radioactive insulin derivatives. In intact cells, insulin stimulates the phosphorylation of the β subunit on serine and tyrosine residues, a phenomenon first observed in rat hepatoma cells and IM9 lymphoblasts[12,13], and then extended to a variety of cell types[14-16]. In vitro, insulin-dependent tyrosine kinase activity[14-22] copurifies with the insulin-binding activity to homogeneity[19,20,23]. The protein kinase activity of the insulin receptor catalyzes both phosphorylation of the β subunit as well as exogenous peptides and proteins[14,21,24-26]. Studies with model peptide substrates indicate that the specificity of the insulin-dependent protein kinase is similar to that of the epidermal growth factor (EGF) receptor kinase and the src family of tyrosine specific protein kinases[24,25]. In addition to being the principal substrate for autophosphorylation, the β subunit bears an ATP binding site[21,22].

The α and β subunits of the heterotetrameric insulin receptor derive from a single, glycosylated, polypeptide precursor of approximately 190,000 daltons[29-31]. Disulfide bridges linking the α and β subunit regions probably begin to form as the protein folds. After being transported from the endoplasmic reticulum to the Golgi apparatus, the precursor is further glycosylated and is then cleaved, followed by its transport to the plasma membrane[27]. Although similar in purported structure to the IGF-1 receptor[28], the insulin receptor differs from the EGF receptor, which functions in the plasma membrane as a single polypeptide chain.

The amino acid sequence of the human EGF receptor was recently reported [32,33]. However, although a need has existed for identifying the DNA encoding the insulin receptor and for expressing the DNA in recombinant culture, and notwithstanding reports of purified human placental insulin receptor in 1981 (7), no sequence information for this complex protein as yet has been disclosed in the literature

SUMMARY

By a novel final purification step we have obtained the human placental insulin receptor in sequenceable grade. Thereafter we determined the nucleotide and imputed complete amino acid sequence of the insulin receptor (also abbreviated herein as "IR" or "HIR" in the case of human insulin receptor). DNA encoding IR or its mutants is expressed in recombinant cells, thereby enabling the synthesis of (a) IR compositions having the amino acid sequence of the natural insulin receptor which are entirely free of other proteins of the species of origin and (b) novel mutant insulin receptors. This DNA or its fragments are useful in the hybridization diagnosis of defective IR DNA or mRNA and for obtaining DNA encoding IR from natural sources. IR and its mutants are therapeutically useful in the treatment of insulin overdose-induced nypoglycemia and in the study of the mechanisms of insulin-dependent cell metabolism. Known polypeptide fragments of IR are useful for generating antibodies in animals which are capable of binding IR in predetermined domains. These antibodies are useful, for example, as therapeutic agents and as components in diagnostic assays for IR and its mutants.

The DNA species provided herein are novel. cDNA which encodes IR is obtained by reverse transcription of mRNA from cells. Accordingly, it contains no introns and is free of any flanking regions encoding other proteins of the organism from which the mRNA originated. Chromosomal DNA encoding IR is obtained by probing genomic DNA libraries with theIR cDNA or its fragments. Chromosomal DNA encoding IR in its entiret.y is excised free of the nonmal chromosomal flanking regions encoding other proteins, but it may contain introns.

The isolated IR DNA is readily modified by substitution, deletion or insertion of nucleotides, thereby resulting in novel DNA sequences encoding IR or its derivatives. These modified sequences are used to produce mutantIR or to enhance the expression of IR species.

In processes for the synthesis of IR, DNA which encodes IR is ligated into a replicable (reproducible) vector, the vector used to transform host cells, the host cells cultured and IR recovered from the culture. The IR species which are capable of synthesis herein include mature (amino-terminal) IR, preIR and IR derivatives including (a) fusion proteins wherein IR or any fragment thereof (including mature IR) is linked to other proteins or polypeptides by a peptide bond at the amino and/or carboxyl terminal amino acids of IR or its fragments, (b) IR fragments, including mature IR or fragments of preIR in which any. preprotein amino acid is the amino-terminal amino acid of the fragment, (c) mutants of IR or its fragments wherein one or more amino acid residues are substituted, inserted or deleted, and/or (d) methionyl or modified methionyl (such as formyl methionyl or other blocked methionyl species) amino-terminal addition derivatives of the foregoing proteins, fragments or mutants.

Ordinarily, mammalian cells are transformed with a vector containing the sequence of mature IR or its fragments or mutants linked at its 5' end to the IR presequence or other secretory leader recognized by eukaryotic cells, the cell cultured, and mature IR, fragments or mutants are recovered from the culture. IR is secreted by expression of an IR mutant in mammalian cells where the transmembrane sequence has been deleted or substituted by a hydrophilic domain.

Also within the scope of this invention are derivatives of IR other than variations in amino acid sequence or glycosylation. Such derivatives are characterized by covalent or aggregative association with chemical moieties. The derivatives generally fall into three classes: Salts, side chain and terminal residue covalent modifications, and adsorption complexes, e.g. with cell membranes.

Antibodies against predetermined fragments of IR are raised by immunization of animals with conjugates of the fragments with immunogenic proteins. Monoclonal antibodies are prepared from cells secreting desired antibody. These antibodies are screened for insulin-like activity on normal or defective receptors.

Recombinant IR or IR antibodies are purified and then combined for therapeutic use with physiologically innocuous stabilizers and excipients, sterile filtered and placed into dosage form as by lyophilization in dosage vials or storage in stabilized aqueous preparations. Within the scope herein are derivatives of antibodies which are not complement binding.

IR compositions are administered to animals in therapeutically effective doses to neutralize excessive circulating insulin, as for example in overdose emergencies. Suitable dosages will be apparent to the artisan in the therapeutic context. Similarly, anti-IR compositions having insulin-like activity are administered as required to induce metabolism of blood glucose.

BRIEF DESCRIPTION OF THE DRAWINGS

FIG. 1a is a schematic diagram of a cDNA clone (λHIR-P12) encoding HIR. Indicated are the single internal EcoRI restriction site, untranslated sequences (-), translated sequences (boxed), signal sequence (hatched), cysteine-rich region (shaded), putative precursor processing site and the transmembrane domain (black bar).

FIG. 1b depicts the nucleotide sequence of the HIR precursor cDNA and its deduced amino acid sequence. Amino acids numbered starting at His (1) of the prereceptor sequence are preceded by a 27-residue signal sequence. The experimentally determined amino-terminal sequences of the insulin receptor α and β subunits are underlined. Emphasized are the putative transmembrane sequence (black bar), consensus sequences for N-linked glycosylation (open bars), cysteine residues (shaded) and the precursor processing site (boxed).

FIG. 2a depicts the Northern hybridization analysis of placental mRNA by Northern blot analysis.

FIG. 2b depicts a Southern blot analysis of placental genomic DNA.

FIG. 4 is a schematic comparison of the insulin and EGF receptors. Regions of high Cys-residue concentration are shown as hatched boxes, transmembrane domains as black boxes, and single cysteine residues, that are possibly involved in formation of the $\alpha 2$ $\beta 2$-insulin receptor complex, as black circles.

Figure 5A:
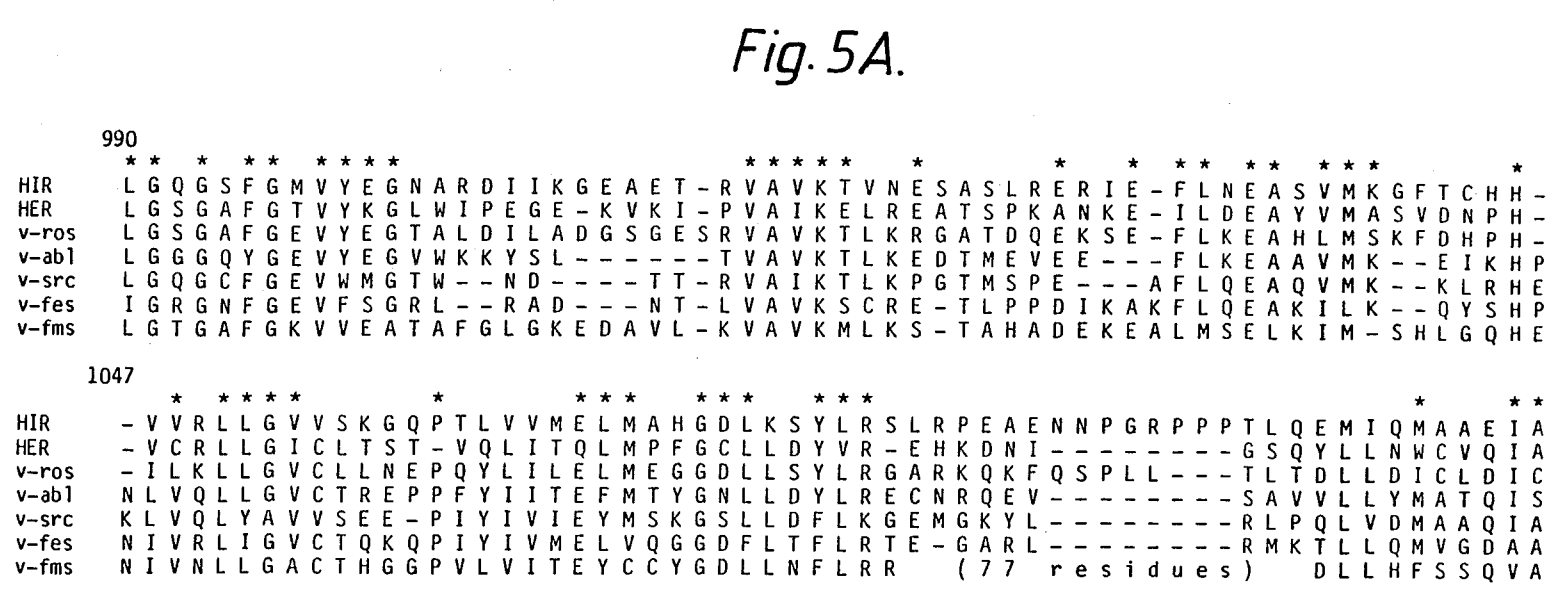
Figure 5B:
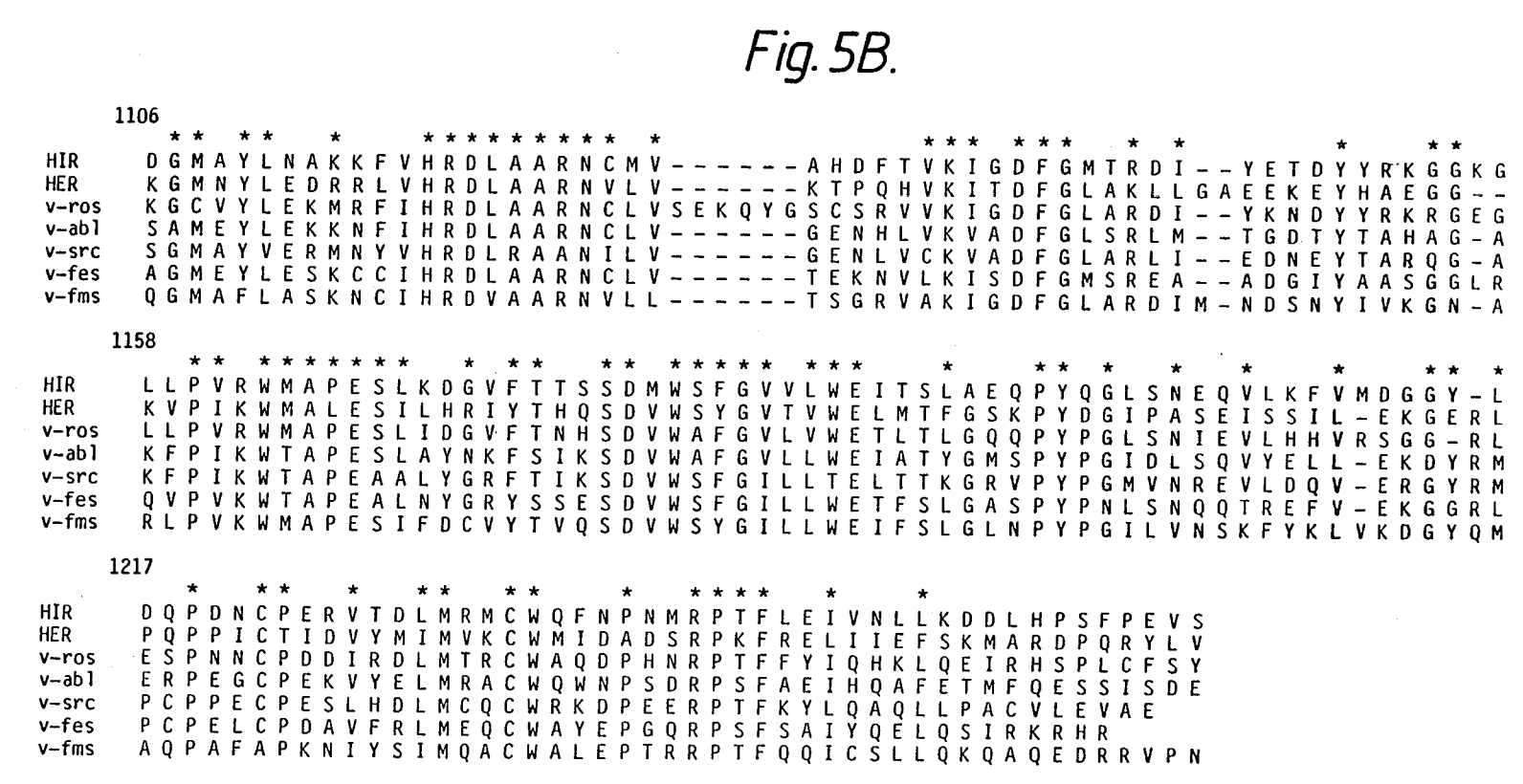

FIG. 5 is a comparison of oncogene and human EGF receptor sequences with that of HIR in the cytoplasmic domain of the insulin receptor beta subunit.

DETAILED DESCRIPTION

Figure 3:
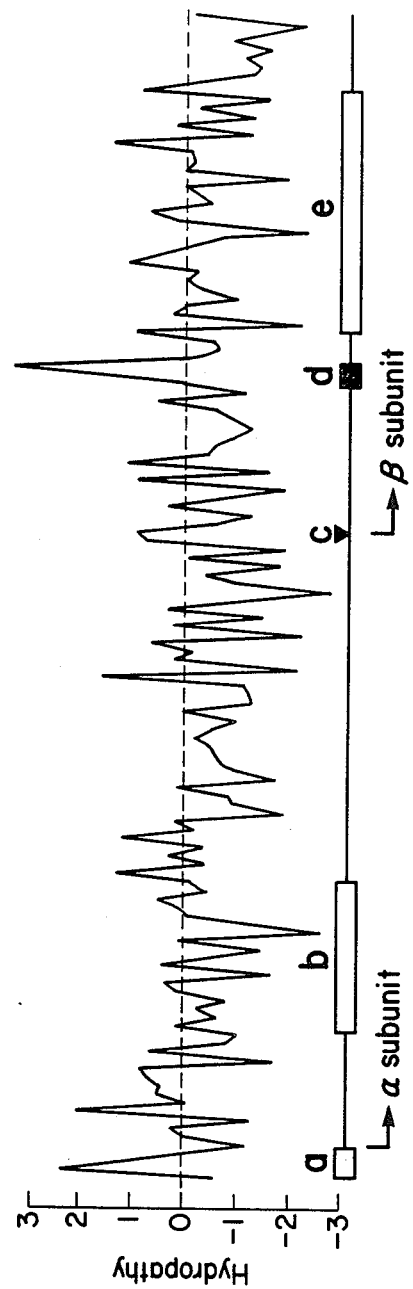
FIG. 3 shows the results of hydropathy analysis of the 1370-amino-acid-long pre-insulin receptor sequence. Landmarks within the sequence are indicated schematically: signal sequence (a), cysteine-rich region (b), precursor processing site (c), transmembrane sequence (d) and tyrosine kinase domain (e).

For the purposes herein, IR is defined as a protein or polypeptide which is substantially homologous with the amino acid sequence depicted in FIG. 1b or a fragment thereof, excluding any protein or polypeptide which exhibits substantially the same or lesser homology to the selected FIG. 1b sequence than does the insulin-like growth factor receptor (IGFR), epidermal growth factor receptor (EGFR) or the oncogenes v-abel, v-svc, v-fes, v-fms, v-ros or v-erb B. Ordinarily insulin receptor polypeptides will be about from 40 to 100 percent homologous to the FIG. 1b sequence, preferably 80 to 90 percent homologous, and they will exhibit at least some biological activity in common with the insulin receptor of FIG. 1b. Biological activity shall include, but is not limited to, insulin binding, ATP binding, protein phosphorylation activity and cross-reactivity with anti-IR antibodies raised against IR from natural (i.e., nonrecombinant) sources. Homology is determined by optimizing residue matches b.y introducing gaps as required but without considering conservative substitutions as matches. This definition is intended to include natural allelic variations in IR sequence.

IR includes the insulin receptors of animals other than humans, e.g. bovine, porcine or ovine.

PreIR is a species of IR included within the foregoing definition. It is characterized by. the presence in the molecule of a signal (or leader) polypeptide which serves to post-translationally direct the protein to a site inside or outside of the cell. Generally, the signal polypeptide (which will not have IR activity in its own right) is proteolytically cleaved from a residual protein having IR activity as part of the secretory process in which the protein is transported into the host cell periplasm or culture medium. The signal peptide may be microbial or mammalian (including the native, 27 residue presequence), but it preferably is mammalian.

Derivatives of IR included herein are amino acid sequence mutants, glycosylation variants and covalent or aggregative conjugates with other chemical moieties. Covalent derivatives are prepared by linkage of functionalities to groups which are found in the IR amino acid side chains or at the N- or C-termini, by means known in the art. These derivatives may, for example, include: aliphatic esters or amides of the carboxyl terminus or residues containing carboxyl side chains, O-acyl derivatives of hydroxyl group-containing residues, and N-acyl derivatives of the amino terminal amino acid or amino-group containing residues, e.g. lysine or arginine. Acyl groups are selected from the group of alkyl-moieties (including C3 to C18 normal alkyl), thereby forming alkanoyl aroyl species.

A major group of derivatives are covalent conjugates of IR or its fragments with other proteins or polypeptides. These derivatives are synthesized in recombinant culture as N- or C-terminal fusions or by the use of difunctional agents known per se for use in cross-linking proteins to insoluble matrices through reactive side groups. Preferred IR derivatization sites with cross-linking agents are at cysteine and lysine residues. Preferred agents are M-Maleimidobenzoyl succinimide ester and N-hydroxysuccinimide.

Covalent or aggregative derivatives are useful as immunogens, reagents in immunoassay or for affinity purification procedures of insulin or other binding ligands. For example, IR is insolubilized by covalent bonding to cyanogen bromide-activated Sepharose by methods known per se or adsorbed to polyolefin surfaces (with or without glutaraldehyde cross-linking) for use in the assay or purification of anti-IR antibodies or insulin. IR also is labelled with a detectable group, e.g., radioiodinated by the chloramine T procedure, covalently bound to rare earth chelates or conjugated to another fluorescent moiety for use in diagnostic assays.

Mutant IR derivatives include the predetermined, i.e. site specific, mutations of IR or its fragments. Mutant IR is defined as a polypeptide otherwise falling within the homology definition for IR as set forth herein but which has an amino acid sequence different from that of IR as found in nature, whether by way of deletion, substitution or insertion. For example, the Arg Lys Arg sequence at residues 720-723, inclusive, may be mutated by deletion (in order to produce a single chain receptor) or by substitution with another proteolysis recognition sequence more compatible with a recombinant host cell. Similarly, the transmembrane sequence, believed to span residues 918-940, inclusive, is deleted or substituted with hydrophilic residues such as serine to facilitate secretion of the receptor into cell culture medium.

While the mutation sites are predetermined, it is unnecessary that the mutation per se be predetermined. For example, in order to optimize the performance of mutants at a given residue position, random mutagenesis may be conducted at the target codon and the expressed IR mutants screened for the desired activity. Techniques for making substitution mutations at predetermined sites in DNA having a known sequence are well known, for example M13 primer mutagenesis.

IR mutagenesis is conducted by making amino acid insertions, usually on the order of about from 1 to 10 amino acid residues, or deletions of about from 1 to 30 residues. Substitutions, deletions, insertions or any subcombination may be combined to arrive at a final construct. Insertions include amino or carboxyl-terminal fusions. Obviously, the mutations in the DNA must not place coding sequences out of reading frame and preferably will not create complementary regions that could hybridize to produce secondary mRNA structure such as loops or hairpins.

Not all mutations in the DNA which encode IR will be expressed in the final product. For example, a major class of DNA substitution mutations are those in which a different secretory leader or signal has been substituted for the native human secretory leader, either by deletions within the leader sequence or by substitutions, wherein most or all of the native leader is exchanged for a leader more likely to be recognized by the intended host. However, the human secretory leader will be recognized by hosts other than human cell lines, most likely in cell culture of higher eukaryotic cells. When the secretory leader is "recognized" by the host, the fusion protein consisting of IR and the leader ordinarily is cleaved at the leader-mature IR peptide bond in the events that lead to secretion of IR or its insertion into the cell membrane. Thus, even though a mutant preIR is synthesized as an intermediate, the resulting IR will be mature.

Another major class of DNA mutants that are not expressed as IR derivatives are nucleotide substitutions made to enhance expression, primarily to avoid amino terminal loops in the transcribed mRNA (see EP 75,444A, incorporated by reference) or to provide codons that are more readily transcribed by the selected host, e.g. the well-known E. coli preference codons for E. coli expression.

Compositions comprising IR may include such substances as the stabilizers and excipients described below, predetermined amounts of proteins from the cell or organism that served as the source of DNA encoding the IR, proteins from other than the IR source cells or organisms, and synthetic polypeptides such as poly-L-lysine. Recombinant IR which is expressed in allogeneic hosts of course will be expressed completely free of gene source proteins. For example, the expression of human IR in CHO or other higher mammalian cells results in a composition where the receptor is not only free of human proteins but the IR in the culture is not denatured, unlike the partially purified HIR preparations reported in the literature.

DNA which encodes IR is obtained by chemical synthesis, by screening reverse transcripts of mRNA from placental cells or cell line cultures, or by screening genomic libraries from any cell.

This DNA is covalently labelled with a detectable substance such as a fluorescent group, a radioactive atom or a chemiluminescent group by methods known per se. It is then used in conventional hybridization assays. Such assays are employed in identifying IR vectors and transformants as described in the Examples infra, or for in vitro diagnosis such as detection of the aberrant IR DNA or mRNA in tissue samples.

IR is synthesized in host cells transformed with vectors containing DNA encoding IR. A vector is a replicable DNA construct. Vectors are used herein either to amplify DNA encoding IR and/or to express DNA which encodes IR. An expression vector is a replicable DNA construct in which a DNA sequence encoding IR is operably linked to suitable control sequences capable of effecting the expression of IR in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (including phage), and integratable DNA fragments (i.e., fragments integratable into the host genome by recombination). The vector replicates and functions independently of the host genome, or may, in some instances, integrate into the genome itself. In the present specification, "vector" is generic to "plasmid", but plasmids are the most commonly used form of vector at present. However, all other forms of vectors which serve an equivalent function and which are, or become, known in the art are suitable for use herein. Suitable vectors will contain replicon and control sequences which are derived from species compatible with the intended expression host. Transformed host cells are cells which have been transformed or transfected with IR vectors constructed using recombinant DNA techniques. Transformed host cells ordinarily express IR, but host cells transformed for purposes of cloning or amplifying IR DNA do not need to express IR. Expressed IR will be deposited in the cell membrane or secreted into the culture supernatant, depending upon the IR DNA selected.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Suitable host cells are prokaryotes, yeast or higher eukaryotic cells. Prokaryotes include gram negative or gram positive organisms, for example *E. coli* or Bacilli. Higher eukaryotic cells include established cell lines of mammalian origin as described below. A preferred host cell is *E. coli* W3110(ATCC 27,325), although other prokaryotes such as *E. coli* B, *E. coli* X1776 (ATCC 31,537), *E. coli* 294 (ATCC 31,446), Pseudomonas species, Bacillus species or Serratia Marcesans are suitable.

Prokaryotic host-vector systems are preferred for the expression of IR fragments that do not require extensive proteolytic and disulfide processing. A plethora of suitable microbial vectors are available. Generally, a microbial vector will contain an origin of replication recognized by the intended host, a promoter which will function in the host and a phenotypic selection gene, for example a gene encoding proteins conferring antibiotic resistance or supplying an autotrophic requirement. Similar constructs will be manufactured for other hosts. *E. coli* is typically transformed using pBR322, a plasmid derived from an *E. coli* species (Bolivar, et al., 1977, "Gene" 2: 95). pBR322 contains genes for ampicillin and tetracycline resistance and thus provides easy means for identifying transformed cells.

Expression vectors should contain a promoter which is recognized by the host organism. This generally means a promoter obtained from the intended host. Promoters most commonly used in recombinant microbial expression vectors include the $\beta$-lactamase (penicillinase) and lactose promoter systems (Chang et al., 1978, "Nature", 275: 615; and Goeddel et al., 1979, "Nature" 281: 544), a tryptophan (trp) promoter system (Goeddel et al., 1980, "Nucleic Acids Res." 8: 4057 and EPO App. Publ. No. 36,776) and the tac promoter [H. De Boer et al., "Proc. Nat'l. Acad. Sci. U.S.A." 80: 21-25 (1983)]. While these are the most commonly used, other known microbial promoters are suitable. Details concerning their nucleotide sequences have been published, enabling a skilled worker operably to ligate them to DNA encoding IR in plasmid or viral vectors (Siebenlist et al., 1980, "Cell" 20: 269). The promoter and Shine-Dalgarno sequence (for prokaryotic host expression) are operably linked to the DNA encoding the IR, i.e., they are positioned so as to promote transcription of IR messenger from the DNA.

Eukaryotic microbes such as yeast cultures may be transformed with IR-encoding vectors. *Saccharomyces cerevisiae*, or common baker's yeast, is the most commonly used among lower eukaryotic host microorganisms, although a number of other strains are commonly available. Yeast vectors generally will contain an origin of replication from the 2 micron yeast plasmid or an autonomously replicating sequence (ARS), a promoter, DNA encoding IR, sequences for polyadenylation and transcription termination and a selection gene. An exemplary plasmid is YRp7, (Stinchcomb et al., 1979, "Nature", 282: 39; Kingsman et al., 1979, "Gene", 7: 141; Tschemper et al., 1980, "Gene", 10: 157). This plasmid already contains the trp1 gene which provides a selection marker for a mutant strain of yeast lacking the ability to grow in tryptophan, for example ATCC No. 44076 or PEP4-1 (Jones, 1977, "Genetics", 85: 12). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., 1980, "J. Biol. Chem.", 255: 2073) or other glycolytic enzymes (Hess et al., 1968, "J. Adv. Enzyme Reg.", 7: 149; and Holland et al., 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol denydrogenase 2, isocytochrome C, acid phosphatase, degradative enzymes associated with nitrogen metabolism, and the aforementioned metallothionein and glyceraldehyde-3-phosphate denydrogenase, as well as enzymes responsible for maltose and galactose utilization. In constructing suitable expression plasmids, the termination sequences associated with these genes are also ligated into the expression vector 3' of the IR coding sequences to provide polyadenylation and termination of the mRNA.

Cultures of cells derived from multicellular organisms are the preferred hosts for recombinant IR synthesis. This is particularly so for mature IR or the IR $\alpha$ or $\beta$ chains as extensive host cell processing is required. In principal, any higher eukaryotic cell culture is workable, whether from vertebrate or invertebrate culture. However, mammalian cells are preferred. Propagation of such cells in cell culture has become a routine procedure in recent years [*Tissue Culture*, Academic Press, Kruse and Patterson, editors (1973)]. Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication (Fiers et al., 1978, "Nature", 273: 113). Smaller or larger SV40 fragments may also be used, provided the approximately 250 bp sequence extending from the Hind III site toward the Bgl I site located in the viral origin of replication is included. Further, it is also possible, and often desirable, to utilize the human genomic IR promoter, control and/or signal sequences, provided such control sequences are compatible with the host cell chosen.

An origin of replication may be provided either by construction of the vector to include an exogenous origin, such as may be derived from SV40 or other viral (e.g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the IR DNA. An example of a suitable selectable marker is dinydrofolate reductase (DHFR) or thymadine kinase. Such markers are proteins, generally enzymes that enable the identification of transformant cells, i.e., cells which were competent to take up exogenous DNA. Generally, identification is by survival of transformants in culture medium that is toxic or from which the cells cannot obtain critical nutrition without having taken up the marker protein. In selecting a preferred host mammalian cell for transfection by vectors which comprise DNA sequences encoding both IR and DHFR, it is appropriate to select the host according to the type of DHFR protein employed. If wild type DHFR protein is employed, it is preferable to select a host cell which is deficient in DHFR thus permitting the use of the DHFR coding sequence as a marker for successful transfection in selective medium which lacks hypoxanthine, glycine, and thymidine, critical nutrients that are not available without DHFR. An appropriate host cell in this case is the Chinese hamster ovary (CHO) cell line deficient in DHFR activity, prepared and propagated as described by Urlaub and Chasin, 1980, "Proc. Natl. Acad. Sci. USA" 77: 4216. This method is further described in U.S. Pat. No. 4,399,216; the procedures therein are adapted here for use in IR synthesis by substitution of DNA encoding an IR species for the genomic or $\beta$-globin DNA used in the cited patent using appropriate synthetic linkers as required.

Note that if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line, CHO-K1 (ATCC No. CCL 61).

Other methods suitable for adaptation to the synthesis of IR in recombinant vertebrate cell culture include those described in M-J. Gething et al., "Nature" 293:620-625 (1981); N. Mantei et al., "Nature" 281:40-46; A. Levinson et al., EP 117,060A and 117,058A.

HIR synthesized in recombinant culture is characterized by the presence of non-human cell components, including proteins, in amounts and of a character which depend upon the purification steps taken to recover HIR from the culture. These components ordinarily will be of yeast, procaryotic or non-human higher eukaryotic origin and and preferably are present in innocuous contaminant quantities, on the order of less than about 1 percent by weight. Further, recombinant cell culture enables the production of IR absolutely free of homologous proteins. Homologous proteins are those which are normally associated with the IR as it is found in nature in its species of origin, e.g. in cells, cell exudates or body fluids. For example, a homologous protein for HIR is human serum albumin. Heterologous proteins are the converse, i.e. they are not naturally associated or found in combination with the IR in question.

IR or anti-IR is prepared for administration by mixing IR or anti-IR having the desired degree of purity with physiologically acceptable carriers. Such carriers will be nontoxic to recipients at the dosages and concentrations employed. Ordinarily, the preparation of such compositions entails combining the IR with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients.

IR compositions are administered to counteract insulin overdose or to adsorb autoimmune anti-IR antibodies. The route of administration is intravenous and dose is measured by amelioration of hypoglycemia, i.e., increases in blood sugar or, in the case of anti-IR antibody therapy, by insulin efficacy. IR compositions used in the emergency therapy for insulin-induced hypoglycemia desirably are combined with conventional agents such as i.v. dextrose used to treat insulin overdose. IR produced by recombinant techniques also is useful in preparing receptor affinity columns for the purification of insulin.

In order to simplify the Examples certain frequently occurring methods may be referenced by shorthand phrases.

Plasmids are designated by a low case p preceded and/or followed by capital letters and/or numbers. The starting plasmids herein are commercially available, are publically available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, and unless otherwise provided, about 1 $\mu$g of plasmid or DNA fragment is used with about 1 unit of enzyme in about 20 $\mu$l of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133-134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9: 6103-6114, and D. Goeddel et al., 1980, "Nucleic Acids Res." 8: 4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98: 503-517, and hybridization as described by T. Maniatis et al., 1978, "Cell" 15: 687-701.

"Transformation" means introducing DNA into an organism so that the DNA is replicable, either as an extrachromosomal element or chromosomal integrant. Unless otherwise provided, the method used herein for transformation of E. coli is the CaCl$_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All literature citations are expressly incorporated by reference.

EXAMPLE 1

N-terminal Amino Acid Sequences and DNA Probe Design

The insulin receptor was purified from human placental membrane preparations by chromatography on wheat germ agglutinin agarose and insulin agarose as described previously[23], except that phenylmethylsulfonyl fluoride (PMSF) was used to inhibit proteolysis; elution from wheat germ agglutinin was performed at 4° C. and the protein was eluted from the insulin column with 0.5 percent SDS. Chromatograpy on hydroxylapatite in SDS[43] was used to concentrate the partially purified receptor as follows. The insulin agarose eluate was diluted to less than 0.2 percent SDS and made 0.01M in sodium phosphate, pH 6.4, and 1 mM in dithiothreitol and passed over a three ml column of hydroxylapatite at 37° C.; bound protein was eluted with 0.6M sodium phosphate, pH 6.4, 1 mM dithiothreitol, 0.1 percent SDS. Purification of the subunits was obtained by preparative polyacrylamide gel electrophoresis after dialysis against 0.1 percent SDS. Samples were electrophoresed on seven percent gels with 1 mM sodium thioglycolate in the upper reservoir buffer, and bands were excised from the Coomassie blue stained gel and electroeluted as described[44]. Quantitation of the alpha and beta subunits was based on a determination of the staining intensity of individual bands with Coomassie blue after polyacrylamide gel electrophoresis. Staining was determined by laser densitometry (Model 2202 Ultroscan, LKB) and the receptor bands were compared with known amounts of standard proteins (myosin, beta galactosidase, and phosphorylase B) run on the same gel. However, particularly in the case of the beta subunit the protein sequence analysis results suggest that our estimate of the amount of receptor is low.

Purified protein was applied to the vapor phase protein sequencer (Model 470A, Applied Biosystems) described by Hewick et al.[45,] and the amino acid derivatives released were determined by reversed phase HPLC on a Microsorb C8 column (4.6×250 mm, Rainin) using an aqueous phosphate buffer with acetonitrile as the organic solvent. In the case of the alpha subunit, 65 pmoles of sequence was obtained from an estimated 130 pmoles of protein, while 400 pmoles of sequence was obtained from an estimated 300 pmoles of the beta subunit. The following are the amino terminal amino acid sequences of the insulin receptor α and β subunits and the nucleotide sequences of the α and β subunit probes designed therefrom. Codons for (XXX) positions were chosen on the basis of tentative amino acid assignments. Parentheses indicate uncertainty in assignment. Asterisks indicate ligation points between independently synthesized oligonucleotides. Underlined nucleotides represent later determined mismatches with the natural insulin receptor cDNA complement.

α Subunit

```
              5            10           15          20
XxxLeuTyrProGlyGlu ValXxx Pro GlyMet AspIleArg AsnXxx LeuThrArgXxxHisGlu

*                        *                    *
CTGTACCCCGGCGAG GTGTGC CCCGGCATG GACATCAGG AACAAC CTGACCAGGTACCACGAG
GACATGGGGCCGCTC CACACG GGGCCGTAC CTGTAGTCC TTGTTG GACTGGTCCATGGTGCTC
              *                        *
```

β Subunit

```
              5           10          15
(Ser)LeuGlyAspValGlyXxx ValThr ValAlaValPro XxxVal AlaAlaPhePro
```

```
CTGGGCGACGTGGGCTGC GTGACC GTGGCCGTGCCC TCCGTG GCCGCCTTCCCC
GACCCGCTGCACCCGACG CACTGG CACCGGCACGGG AGGCAC CGGCGGAAGGGG
```

The double stranded nybridization probes were prepared using an automatic DNA synthesizer (Biosearch). Short overlapping oligonucleotides were synthesized and purified by acrylamide gel electrophoresis. Approximately 10 pmol of each oligonucleotide were phosphorylated in separate reactions using three-fold excess of $\gamma^{32}$P-ATP (Amersham) and T4 polynucleotide kinase. Full-length probes were prepared by combining the 5′ end labeled oligonucleotides and ligation with 2 units of T4 DNA ligase at 20° C. for 2 hrs. Analytical examination of the ligation result demonstrated that about 69–80 percent of the DNA had been ligated to probe monomer size. The entire ligation mixture was boiled to separate DNA strands and used for nybridization as described[37].

EXAMPLE 2

Identification of cDNA Which Encodes IR

Total polyA-containing RNA was isolated from frozen term placenta. A clone library ($1.5 \times 10^6$ pfu) with cDNA (>500 bp) and the λgt10vector system was prepared as described[33,34].

Initial screening with the α-subunit probe detected 15 hybridization positive recombinant phage. Characterization of purified phage DNAs by EcoRI restriction analysis followed by Southern blot hybridization[35] showed that each clone contained two EcoRI fragments, one of which hybridized with the synthetic α subunit probe. Only one phage (λHIR-P12) contained a second EcoRI fragment that hybridized with the β subunit probe. The entire cDNA insert of phage λHIR-P12 measured about 5 kb (1 kb and 4 kb EcoRI fragments, FIG. 1a) and was therefore large enough to code for the entire human insulin receptor precursor, estimated to be approximately 190,000 daltons including carbonydrate side chains[31].

Nucleotide sequence analysis confirmed that the 1 kb EcoRI fragment contained an open reading frame which coded for the amino terminal sequence of the insulin receptor α subunit. The leucine residue which we had determined to be located at position two of the mature α-subunit was found to be preceded by a histidine. An initiation ATG codon was identified 27 amino acids upstream from His (1), flanked by nucleotides which match Kozak's[36] criteria for a translation initiation site. The amino acid residues between the ATG codon and the NH$_2$-terminus of the mature protein are highly hydrophobic, and are believed to represent the signal peptide sequence necessary for transport of the nascent insulin receptor precursor polypeptide into the lumen of the endoplasmic reticulum. B Even though the remaining nucleotide sequence upstream from methionine -27 does not contain any in-frame stop codons, the presence of an adjacent, suitable signal sequence led us to propose that the ATG at position -27 is used for translation initiation. This assignment predicted the orientation of the α and β subunit sequences within the insulin receptor precursor: the α subunit of the receptor was expected to be located upstream from the NH$_2$-terminus of the β subunit within their common precursor. This prediction was confirmed by determination of the complete 5,181 bp long nucleotide sequence of the λHIR-P12 cDNA insert (FIG. 1B). The longest open reading frame starting with methionine within this sequence codes for 1,370 amino acids including the 27 residue signal peptide. The coding sequence is preceded by 50 nucleotides of 5′ untranslated sequence and is followed by a signal for translational termination (TAA) and 1,018 nucleotides of 3′ untranslated sequence. It is not certain that the A-stretch at the 3′ end of our sequence represents part of a polyA tail or an internal sequence within a larger 3′ untranslated region, since this A-stretch is preceded by an imperfect polyadenylation signal (AATATA). To resolve this question, three additional, independent cDNAs representing 3′ untranslated sequences were selected from the placental library and compared by restriction analysis with λHIR-P12 EcoRI fragments. Each of them appeared to end with the same 3′ terminal sequence and matched λHIR-P12 restriction patterns, although none of them extended as far upstream.

Comparison of final cDNA-derived nucleotide sequences with our synthetic probes revealed that the α subunit N-terminal probe contained 9 mismatches (86 percent match) with the longest stretch of perfect match being 11 bp, and the 57 bp, β subunit N-terminal probe contained 12 mismatches (79 percent match) and a 12 bp maximum uninterrupted match. No false positives were identified.

Based on our cDNA sequence we calculated molecular weights of 155,000 for the pre-insulin-receptor-precursor and 152,000 for the mature precursor. A tetrapeptide (ArgLysArgArg) at position 720 of the insulin receptor precursor sequence directly precedes the β subunit N-terminal sequence (FIG. 1b) and is believed to represent the cleavage site for the receptor precursor processing enzyme. Omitting this peptidase recognition sequence, the final unmodified subunit molecular weights are predicted to be 82,400 (α) and 69,700 (β).

Hydropathy analysis was conducted by scanning the 1370-amino-acid-long pre-insulin receptor precursor sequence using the computer program of Kyte and Doolittle[46]. Landmarks within the sequence are indicated schematically: signal sequence (a), cysteine-rich region (b), precursor processing site (c), transmembrane sequence (d) and tyrosine kinase domain (e). Hydrophobicity results in positive and hydrophilicity in negative values (see Kyte and Doolittle[46]). The results are shown in FIG. 3.

The 719-residue-long α subunit sequence (FIG. 1b) is largely hydrophilic (FIG. 3) with a few short hydrophobic stretches, none of which are long enough to qualify as potential membrane anchor sequences. Fifteen consensus sequences for asparagine-linked glycosylation (Asn $\times$ Ser/Thr) are evenly distributed over the 719-residue-long α subunit region, which is also characterized by an unusually large number (37) of cysteine residues. Twenty-six of the cysteines are concentrated between residues 155 and 312 (FIG. 1b) and are contained within a rather hydrophilic domain (FIG. 3). Although in most cases there is no direct evidence as to which of the potential asparagine-linked carbohydrate attachment sites are in fact glycosylated, our failure to detect the asparagines at positions 16 and 7 of the alpha and beta subunits, respectively, during protein sequencing strongly suggests that these two sites are glycosylated.

The 620-amino-acid-long β subunit sequence contains only nine cysteine residues (1.5 percent) and can be divided into 3 domains. The amino-terminal 194-residue-long domain contains 4 potential asparagine-linked glycosylation sites and four cysteine residues. An adjacent stretch of 23-26 highly hydrophobic amino acids (915 or 918 - 940) is believed to represent the single transmembrane domain that anchors the insulin receptor in the membrane. The transmembrane sequence is flanked at its C-terminal end by three basic amino acids (ArgLysArg; FIG. 1b), which are part of the 403-residue-long carboxy terminal domain that contains two potential N-linked glycosylation sites as well as a typical number of cysteine residues.

EXAMPLE 3

Multiple Related mRNAs

Northern blot analysis[38] was undertaken for polyA+RNA (5 μg) isonated from mouse 3T3-LI fibroblasts before (a) and after differentiation into adipocytes[40] (b) and human term placenta tissue (c) after separation on a formaldehyde-containing one percent agarose gel and transfer to nitrocellulose. Rat ribosomal RNA was used as a size marker. The filter was hybridized with radiolabelled insulin receptor cDNA fragments[47] (1010 bp and 4169 bp EcoRI). Exposure was for 3 days at $-60°$ C. using an intensifying screen (Cronex Lightning Plus). Additional Northern blot experiments with placenta and IM-9 RNAs were carried out as mentioned in the text. The following cDNA fragments were used in parallel experiments: EcoRI 1-1011; EcoRI 1012-XhoI 2904; StuI 3234-StuI 3728; StuI 2399-XhoI 3080; PstI 4341-EcoRI 5169.

Northern blot hybridization[38] analysis using polyA+RNA from term placenta, as well as fetal placenta (20 week) and a human lymphoblast cell line (IM-9), yielded a complex pattern of five common hybridization bands, 8.2 kb, 7.3 kb, 6.5 kb, 5.5 kb and 4.6 kb in length (FIG. 2A). A faint, 2.9 kb band was also detected, but was present only in term placenta and IM-9 RNAs. The hybridization signal intensities for the bands was different for each band, indicating that either variable amounts of different length mRNAs are synthesized from the same gene, or that different but related genes are transcribed to yield multiply-sized mRNAs. To further investigate the identity of mRNAs from placenta and IM-9 cells which hybridize with our 5.2 kb insulin receptor cDNA probe, we used a variety of cDNA probe fragments as hybridization probes in Northern blot hybridization experiments. In all cases, at least all of the four largest transcripts (8.2, 7.3, 6.5 and 5.5 kb) were detected.

After treatment with dexamethasone and isobutyl methylxanthine, mouse 3T3-LI fibroblasts differentiate into adipocytes, in a process which leads to a ten to twenty fold increase in the number of insulin receptor molecules on their surfaces.[39,40] Northern blot analysis carried out with polyA-containing mRNA obtained from these cells before and after differentiation revealed that the increase in receptor molecules parallels an approximately tenfold increase in two insulin receptor mRNAs (FIG. 2A, a and b). Unlike the complex transcription pattern observed in placenta (FIG. 2A, C), the 3T3-LI cells synthesized only comparable amounts of a 6.5 and an 8.2 kb mRNA, both before and after induction. These experiments strongly suggest that the major transcripts of 6.5 and 8.2 kb represent insulin receptor mRNAs. The mRNAs may differ in the lengths of their 3' or 5' untranslated sequences, as has been described for other gene systems[41,42] or alternatively these mRNAs could be generated by variable splicing of a primary transcript from the same gene.

EXAMPLE 4

DNA Probe Analysis of Genomic DNA

To determine the number of insulin receptor genes present in the human genome, Southern blot analyses[35] were carried out using an 857 bp PstI-EcoRI cDNA fragment derived from the 3' most terminal untranslated sequence as a hybridization probe. High molecular weight DNA (10 μg per lane) isolated from placental nuclei was digested with excess amounts of EcoRI (a), HincII (b), and PstI (c), separated on a one percent agarose gel and analyzed by Southern blot hybridization[35]. The radiolabelled probe used under high stringency conditions consisted of a 857 bp 3' terminal PsI-EcoRI fragment. λ wt phage DNA digested with EcoRI and HindIII was used as size marker. These sequences were chosen because they are the most rapidly divergent sequences within gene families and would therefore avoid detection of closely related genes. As can be seen in FIG. 2B, this probe hybridized with single restriction fragments from high molecular weight, nuclear DNA, consistent with the presence of only one insulin receptor gene in the haploid human genome.

EXAMPLE 5

Expression of HIR in Mammalian Cells

A gel purified SalI fragment (~5.2 kb) from λHIR-P12 containing the entire HIR coding sequence was subcloned into the pUC12 (New England Biolabs) polylinker region by digesting pUC12 with SalI and ligating the purified SalI fragment to the vector. Plaques were grown up and screened for clones having the desired XbaI-SalI-HIR-SalI-HindIII orientation (where the XbaI and HindIII sites originate from the pUC12 polylinker and flank the SalI inserted HIR gene). This vector was designated PUC12/HIRc. pUC12/HIRc was cut with XbaI and DraI (DraI is located in the 3' untranslated region of HIR) and the HIR-containing fragment was isolated. This fragment was inserted into a mammalian expression vector (pCVSVEHBVE400, European Publn. No. 117060), which had been digested first with BamHI. The BamHI expression vector sticky ends were filled in with Klenow PolI and subsequently the plasmid was digested with XbaI. Thus, insertion of the XbaI-DraI was only possible in the orientation necessary for expression of the HIR mRNA. The resulting insulin receptor expression plasmid was designated pCVSVE-HIRc-2. It is subsequently transfected by standard procedures into several mammalian cell lines such as MDCK, CHO, Rat1 (a rat fibroblast cell line) or COS and cultured in transient expression culture medium under conditions favoring transient expression as are generally known in the art. Stable transformants are identified by culture in medium to select for DHFR expression from pCVSVE-HIRc-2. Transient expression is measured after about 40 hrs by binding of radioiodinated insulin to transfected vs. nontransfected control cells.

EXAMPLE 6

Expression of Mutant HIR in Mammalian Cells

This example describes the method generally usable for deletional mutagenesis of IR. The following embodiment describes the deletion of the transmembrane region (TMR) of HIR.

The gel purified SalI fragment from Example 5 is ligated to SalI digested M13mp8 replicative form DNA (J. Adelman et al., 1983, "DNA" 2 (3):183-193) and transfected into *E.coli* JM103. Transformants (pSal-HIR) are identified as described in Adelman et al., op cit.

The synthetic oligodeoxyribonucleotides 5'GCTGCCTCTTTCTTTTTGCAATATTTG-3' ("Δ") (complementary to the HIR coding regions immediately proximal and distal to the TMR), 5'GAAGT-CACAACACTAACCTTC3' ("loop") (complementary to a portion of the TMR), 5'AGAAGC-GTAAAGCGGTCC3' (a sequencing primer complementary to the region enclodging HIR amino acid residues 950-955) and 5'GTTTTCCCAGTCACGAC3' ("LAC", regularly used as a sequencing primer on recombinant phage M13 DNA) were prepared by the method of Crea et al., "Nucl. Acids Res." 8:2331-2348 (1980).

The oligonucleotides were phosphorylated as described in Adelman et al., op cit.

Phosphorylated Δ and LAC are annealed to pSalHIR and primer extended as described in Adelman et al., op cit. DNA is recovered as described and used to transform *E.coli* JM103. Transformant phage are identified by screening with "loop" and Δ. A transformant having the transmembrane region deletion (designated pSal-HIRd918-940) is identified by DNA sequence analysis using the sequencing primer described above in the method of Adelman et al., op cit. DNA is recovered from pSalHIRd918-940 and digested with SalI. The mutant HIR DNA is recovered and ligated to SalI digested pUC12 as described above in Example 5. Thereafter, Example 5 is repeated except that expression is measured by an HIR sandwich immunoassay of the cell culture supernatant using immobilized and labelled polyclonal antisera raised against HIR (host cell IR will be cell membrane bound and antisera are used in the assay which are selected for low titer cross-reactivity with the host cell IR).

Other deletional, substitution and insertional mutations e.g. mutations of residues 720-723, are prepared in similar fashion and/or by the use of synthetic oligonucleotide inserts using the methods of U.S. patent application No. 614,617; U.K. patent application No. 2,130,219A; R. Wallace et al., 1981, "Nucleic Acids Research" 9 (15): 3647-3656; G. Winter et al., 1982, "Nature" 299: 756-758; and A. Hui et al., 1984, "The EMBO Journal" 3 (3): 623-629), all of which are expressly incorporated herein.

EXAMPLE 7

Preparation of Antibodies Against Predetermined Amino Acid Sequences of IR

In this contemplated example, the peptides described in the following Table I are synthesized by the Merrifield solid phase synthesis technique (68) and conjugated to the proteins scheduled in Table I using the indicated bifunctional agents in accord with conventional practice.

TABLE I

| Polypeptides (designated by HIR residues, inclusive) | Conjugating Agent | Protein |
|---|---|---|
| 147-158 | MBS[a] | keyhole limpet hemocyanin (KLH) (Calbiochem) |
| 158-168 and/or 320-334 | MBS | KLH |
| 175-187 | MBS | KLH |
| 267-282 | NHS[b] | KLH |
| 166-177 and/or 275-287 | NHS | KLH |
| 149-163 and/or 134-149 | NHS | KLH |
| 241-252 | MBS | bovine serum albumin (BSA) |
| Cys(345-359)[c] | MBS | BSA |
| 120-133 and/or 309-325 | MBS | BSA |
| 179-190 and/or 495-508 | NHS | BSA |
| 197-206 and/or 433-446 | NHS | BSA |
| 193-206 | MBS | soybean trypsin inhibitor (STI) |
| 2-20 and/or 524-535 | MBS | STI |
| 704-720 and/or 724-736 | MBS | STI |
| 954-966 and/or 1142-1154 | MBS | STI |
| 1330-1343 | MBS | STI |
| 183-191 | MBS | bovine thyraglobulin (BT) |
| 319-322 and/or 213-224 | NHS | BT |
| 90-112 and/or 310-324 | NHS | BT |

[a]MBS: m-Maleimidobenzoyl sulfosuccinimide ester. Conjugation is through cysteine residues.
[b]NHS: N—hydroxysuccinimide. Conjugation is through lysine residues.
[c]The indicated polypeptide is synthesized with an added N-terminal cysteine.

Other bifunctional cross-linking agents are known and useable in the preparation of immunogenic conjugates. Examples include glutaraldehyde, succinic anhydride, $SOCl_2$, and $R'N=C=NR$.

Other proteins than those enumerated above are useful. They preferably will be heterologous to the species to be immunized, otherwise the immune response likely will be of low titer if at all.

Preferably, the IR polypeptide fragments chosen are selected from the α subunit, although fragments from the ATP binding, protein phosphokinase and autophosphorylation regions of the receptor are included within the scope hereof.

Animals are immunized against the immunogenic conjugates by combining 1 mg or 1 μg of conjugate (for rabbits or mice, respectively) with 3 volumes of Freund's complete adjuvant and injecting the solution intradermally at multiple sites. One month later animals are boosted with 1/5 to 1/10 the original amount of conjugate in Freund's complete adjuvant by subcutaneous injection at multiple sites. 7 to 14 days later animals are bled and the serum assayed for anti-HIR titer. Animals are boosted until the titer plateaus. Preferably, the animal is boosted with the conjugate of the same IR polypeptide, but conjugated to a different protein and/or through a different crosslinking agent.

Monoclonal antibodies are prepared by recovering spleen cells from immunized animals and immortilizing the cells in conventional fashion, e.g. by fusion with myeloma cells or by EB virus transformation and screening for clones expressing the desired antibody.

Antibodies which are capable of binding to or in the steric vicinity of the IR insulin binding site are identified by immobilizing rabbit anti-IR β-subunit on goat anti-rabbit IgG-coated microtiter wells, adding dilutions of test sample in $^{125}I$-insulin-containing PBS to the coated wells, incubating overnight, aspirating the test sample from the wells, washing with PBS, and determining the radioactivity remaining in the wells by gamma counting. Test samples containing desired antibodies are indicated by increases in insulin displacement at higher sample concentrations.

Similar assays are conducted to identify antibodies which bind to the ATP-binding, protein phosphokinase active site, and autophosphorylation domains of IR.

Diabetes is believed to be primarily a function of inadequate insulin levels or defective or insufficient insulin receptors. For example, an insulin receptor may be defective because of an inability to bind insulin in a fashion that will activate the tyrosine kinase activity of the receptor. This may result, for example, from dominant point mutations in the insulin receptor binding region of IR.

Knowledge of the amino acid sequence for IR has now made possible the generation of antibodies against selected regions of the receptor which can be methodically screened for insulin-like or insulin agonist activity. Such antibodies or their derivatives are useful as insulin substitutes for the therapeutic treatment of diabetes stemming from defective receptor binding of insulin. While anti-insulin receptor antibodies are known that induce glucose uptake by test cells[50], the method herein makes it possible to raise such antibodies against predetermined sites on the IR molecule, thereby avoiding the generation of contaminant antibodies having undesirable side effects[51,52], and for the first time disclose methods for stimulating defective insulin receptors.

Suitable candidate antibodies such as those prepared above, are screened by preparing IR in conventional fashion from a tissue sample obtained from a diabetic patient found partly or wholly refractory to insulin. It is unnecessary to purify the IR to the sequenceable grade described elsewhere herein. It is satisfactory to purify the IR by known methods up to insulin affinity adsorption (which in any case probably would be ineffective where the defective receptor is incapable of binding insulin).

The IR preparation is combined in aqueous solution with (a) 0.1-5 mg/ml of a protein tyrosine kinase substrate such as (Glu AlaTyr)n[49] or histone H2B, (b) (gamma-$^{32}$P) ATP and (c) aliquots of test sample and varying dilutions of the test sample candidate antibody in control antibody solution so as to prepare a curve in which essentially the same antibody concentration is present for each data point. The assay is conducted generally as described previously[49], except that the IR need not be immobilized. Normal antibody from the animal species in which the candidate antibody was raised was prepared in the same way as the candidate antibody to serve as a negative control. Afterincubation the proteins in the solution are precipitated and washed free of labelled ATP, or otherwise separated from labelled ATP as for example by gel electrophoresis. The radioactivity found in the protein fractions from the varying antibody dilutions and negative control is compared. Candidate antibody which induces or stimulates incorporation of $^{32}$P into protein is suitable for therapeutic use as an insulin substitute. Altenatively, a less direct assay will be the measurement of cellular glucose uptake rates in the presence of dilutions of the candidate antibody.

It is prefered to use the Fab fragments of the selected antibody because such fragments, even though divalent, will not bind complement and therefore will not participate in potentially toxic autoimmune responses. Such fragments are obtained by enzymatic digestion of the antibody using conventional methods.

CITATIONS

1. Czech, M. P. Ann. Rev. Biochem. 46, 359-384 (1977).
2. Kahn, C. R. Trends Biochem. Sci. 4, 263-266 (1979).
3. Cobb, M. H. and Rosen, O. M. Biochem. Biophys. Acta 738, 1-8 (1984).
4. Massague, J., Pilch, P. and Czech, M. P. Proc. Natl. Acad. Sci. USA 77, 7137-7141 (1980).
5. Massague, J., Pilch, P. and Czech, M. P. J. Biol. Chem. 256, 3182-3190 (1981).
6. Cuatrecasas, P. J. Biol. Chem. 248, 3528-3534 (1973).
7. Siegel, T., Ganguly, S., Jacobs, S., Rosen, O. M., and Rubin, C. S. J. Biol. Chem. 256, 9266-9273 (1981).
8. Hedo, J., Kasuga, M., Van Obberghen, E., Roth, J., and Kah, C. R. Proc. Natl. Acad. Sci. USA 78, 4792-4795 (1981).
9. Yip, C. C., Yeung, C. W. T. and Moule, M. C. J. Biol. Chem. 253, 1743-1745 (1978).
10. Jacobs, S., Hazum, E., Schechter, Y. and Cuatrecasas, P. Proc. Natl. Acad. Sci. USA 76, 4918-4921 (1979).
11. Pilch, P. F. and Czech, M. J. Biol. Chem. 254, 3375-3381 (1979).
12. Kasuga, M., Karlsson, F. A. and Kahn, C. R. Science 215, 185-187 (1982).
13. Kasuga, M., Zick, Y., Blithe, D. L., Karlsson, F. A., Haring, H. U. and Kahn, C. R. J. Biol. Chem. 257, 9891-9894 (1982).
14. Petruzzelli, L. M., Ganguly, S., Smith, C. S., Cobb, M. H., Rubin, C. S., and Rosen, O. M. Proc. Natl. Acad. Sci. USA 79, 6792-6796 (1982).
15. Van Obberghen, E. and Kowalski, A. FEBS Lett. 143, 179-182 (1982).
16. Haring, H. U., Kasuga, M., and Kahn, C. R. BBRC 108, 1538-1545 (1982).
17. Zick, Y., Kasuga, M., Kahn, C. R., and Roth, J. J. Biol. Chem. 258, 75-80 (1983).
18. Avruch, J., Nemenoff, R. A., Blackshear, P. J., Pierce, M. W., and Osothanondh, R. J. Biol. Chem. 257, 15162-15166 (1982).
19. Roth, R. A. and Cassell, D. J. Science 219, 299-301 (1983).
20. Kasuga, M., Fujita-Yamaguchi, Y., Blithe, D. L., and Kahn, C. R. Proc. Natl. Acad. Sci. USA 80, 2137-2141 (1983).
21. Shia, M. A. and Pilch, P. F. Biochemistry 22, 717-721 (1983).
22. Van Obberghen, E., Ross, B., Kowalski, A., Gazzano, H., and Ponzio, G. Proc. Natl. Acad. Sci. USA 80, 945-949 (1983).
23. Petruzzelli, L. M., Herrera, R., and Rosen, O. M. Proc. Natl. Acad. Sci. 81, 3327-3331 (1984).
24. Stadtmauer, L. and Rosen, O. M. J. Biol. Chem. 258, 6682-6685 (1983).
25. Pike, L. J., Kuenzel, E. A., Casnellie, J. E., and Krebs, E. G. J. Biol. Chem. 259, 9913-9921 (1984).
26. Zick, Y., Whittaker, J., and Roth, J. J. Biol. Chem. 258, 3431-3434 (1983).
27. Jacobs, S. and Cuatrecasas, P. Ann. Rev. Pharmacol. and Toxicol. 23, 461-479 (1983).
28. Massague, J. and Czech, M. P. J. Biol. Chem. 257, 5038-5045 (1982).
29. Deutsch, P. S., Wan, C. F., Rosen, O. M., and Rubin, C. S. Proc. Natl. Acad. Sci. USA BO, 133-136 (1983).
30. Hedo, J. A., Kahn, C. R., Hayashi, M., Yamada, K. M., and Kasuga, M. J. Biol. Chem. 259, 9913-9921 (1983).

31. Ronnett, G. V., Knutson, V. P., KohansKy, R. A., Simpson, T. L., and Lane, M. D. J. Biol. Chem. 259, 4566–4575 (1984).
32. Downward, J., Yarden, Y., Mayes, E., Snoer, G., Totty, N., Stockwell, P., Ullrich, A., Schlessinger, J., and Waterfield, M.1. Nature 307, 521–527 (1984).
33. Ullrich, A., Coussens, L., Hayflick, J. S., Dull, T. J., Gray, A., Tam, A. W., Lee, J., Yarden, Y., Libermann, T. A., Schlessinger, J., Downward, J., Mayes, E. L. V., Whittle, N., Waterfield, M. D., and Seeburg, P. H. Nature 309, 418–425 (1984).
34. Huynh, T., Young, R. and Davis, R. in *Practical Approaches in Biochemistry* (ed. Grover, D.) (IRL, Oxford, 1984).
35. Southern, E. J. Molec. Biol. 98, 503–517 (1975).
36. Kozak, M. Nucleic Acids Res. 9, 5233–5252 (1981).
37. Ullrich, A., Berman, C. H., Dull, T. J., Gray, A. and Lee, J. M. EMBO J. 3, 361–364 (1984).
38. Lehrach, H., Diamond, D., Wozney, J. M. and Boedtker, H. Biochemistry 16, 4743–4751 (1977).
39. Rubin, C. S., Hirsch, A. H., Fung, C. and Rosen, O. M. J. Biol. Chem. 253, 7570–7578 (1978).
40. Karlsson, F. A., Grunfeld, C., Kahn, C. R. and Roth, J. Endocrinology 104, 1383–1390 (1979).
41. Tosi, M., Young, R. A., Hagenbuchle, 0. and Schibler, U. Nucleic Acids Res. 9, 2313–2323 (1981).
42. Setzer, D. R., McGrogan, M., Nunberg, J. H. and Schimke, R. T. Cell 22, 361–370 (1980).
43. Moss, B. and Rosenblum, E. N. J. Biol. Chem. 247, 5194–5198 (1972).
44. Hunkapiller, M. W., Lujan, E., Ostrander, F., and Hood, L. E. in Methods in Enzymology Vol. 91 (eds. Hirs, C. H. W. and Timasheff, S. N.) 227–236 (Academic Press, New York, 1983).
45. Hewick, R. M., Hunkapiller, M.W., Hood, L. E. and Dreyer, W. J. J. Biol. Chem. 256, 7990–7997 (1981).
46. Kyte, J. and Doolittle, R. F. J. Mol. Biol. 157, 105–132 (1982).
47. Taylor, J. M., Illmensee, R. and Summers, J. Biochim. biophys. Acta 4, 324–330 (1976).
48. Merrifield, R., J. Am. Chem. Soc. 85, 2149–2154 (1963).
49. Braun, S. et al., J. Biol. Chem. 259, 2051–2054 (1984).
50. Jacobs, S. et al., Science 200, 1283–1284 (1978).
51. Flier, J. et al., Science 190, 63–65 (1975)
52. Kahn, C. et al., J. Clin. Invest. 60, 1094–1106 (1977).

We claim:

1. Isolated DNA encoding an insulin receptor or a fragment thereof encoding a biologically active insulin receptor polypeptide.
2. Isolated DNA which encodes a biologically active insulin receptor and which is capable of hybridizing with the DNA of FIG. 1B.
3. An oligonucleotide probe that is capable of hybridizing with DNA that encodes an insulin receptor and which is labelled with a detectable moiety.
4. A vector comprising DNA encoding an insulin receptor of a fragment thereof encoding a biologically active insulin receptor polypeptide.
5. The vector of claim 4 wherein the DNA is under the control of a viral promoter.
6. The vector of claim 4 additionally comprising DNA encoding a selection marker.
7. The vector of claim 6 wherein the marker is dihydrofolate reductase.
8. The vector of claim 4 wherein the DNA encodes a predetermined, site-specific mutant insulin receptor which is greater than about 40 percent homologous with the insulin receptor of FIG. 1b and which exhibits a biological activity in common with the insulin receptor of FIG. 1b.
9. The vector of claim 8 wherein the transmembrane sequence of the receptor is deleted.
10. A cell from a multicellular organism transformed with the vector of claim 4.
11. The cell of claim 10 which is a mammalian cell.
12. A method comprising culturing the cell of claim 10 in a nutrient medium, permitting the receptor to accumulate in the culture and recovering the receptor from the culture.
13. The method of claim 12 wherein the receptor is recovered from the culture medium.

* * * * *